United States Patent [19]

Fujita et al.

[11] 4,012,146
[45] Mar. 15, 1977

[54] TWO WAVE LENGTH, SCANNING AND INTEGRATION TYPE METHOD OF MICROSPECTROPHOTOMETRICALLY MEASURING THE LIGHT ABSORBANCY OF A SPECIMEN AND MICROSPECTROPHOTOMETER FOR AUTOMATICALLY CARRYING OUT THE METHOD OF MEASUREMENT

[75] Inventors: Setsuya Fujita, Kyoto; Ichiro Sawamura, Hachioji, both of Japan

[73] Assignee: Olympus Optical Co., Ltd., Tokyo, Japan

[22] Filed: Dec. 19, 1973

[21] Appl. No.: 426,240

[30] Foreign Application Priority Data

Dec. 20, 1972 Japan ............................ 47-127097

[52] U.S. Cl. ................................. 356/96; 356/205
[51] Int. Cl.[2] ......................................... G01J 3/42
[58] Field of Search .............. 356/39, 51, 96, 97, 356/201, 204, 205

[56] References Cited

UNITED STATES PATENTS

| 3,781,112 | 12/1973 | Groner et al. | 356/39 |
| 3,811,781 | 5/1974 | Lowy | 356/97 X |
| 3,813,168 | 5/1974 | Honkawa | 356/97 |
| 3,887,281 | 6/1975 | Kurita et al. | 356/96 |

Primary Examiner—John K. Corbin
Assistant Examiner—F. L. Evans
Attorney, Agent, or Firm—Haseltine, Lake & Waters

[57] ABSTRACT

A two wave length, scanning and integration type method of microspectrophotometrically measuring the light absorbancy of a specimen dyed with a coloring matter comprising scanning the specimen by light spots having two different wave lengths and integrating electric signals converted from the light spots traversing the specimen. The two different wave lengths $\lambda_1$ and $\lambda_2$ are selected such that at the wave length $\lambda_1$ the light absorbancy of the absorption spectrum of the coloring matter is maximum and that at the wave length $\lambda_2$ the light absorbancy is zero and the wave length $\lambda_2$ is deviated from the absorption spectrum and located near the wave length $\lambda_1$. A true light absorbancy in proportion to the amount of light absorbing substance at that part of the specimen which is to be measured is obtained by subtracting the light absorbancy produced by the light loss not peculiar to the specimen and caused by the light diffusion due to light reflection, refraction and diffraction in the specimen from the light absorbancy peculiar to the specimen. A two wave length, scanning and integration type microspectrophotometer for automatically carrying out the method of measurement is also disclosed.

2 Claims, 5 Drawing Figures

FIG_1

FIG_2

FIG_3

FIG_5

TWO WAVE LENGTH, SCANNING AND INTEGRATION TYPE METHOD OF MICROSPECTROPHOTOMETRICALLY MEASURING THE LIGHT ABSORBANCY OF A SPECIMEN AND MICROSPECTROPHOTOMETER FOR AUTOMATICALLY CARRYING OUT THE METHOD OF MEASUREMENT

This invention relates to methods of microspectrophotometrically measuring light absorbancy of a specimen and more particularly to a two wave length, scanning and integration type method of microspectrophotometrically measuring the light absorbancy of the specimen comprising scanning the specimen by light spots having two different wave lengths and integrating electric signals converted from the light spots transversing the specimen, and to a two wave length, scanning and integration type microspectrophotometer for automatically carrying out the method of measurement.

As conventional methods of microspectrophotometrically measuring light absorbancy of a specimen, the following four methods have heretofore been proposed.

1. One wave length and one region method,
2. One wave length and two region method,
3. Two wave length method, and
4. One wave length, scanning and integration method.

In the one wave length and one region method (1), use is made of a light spot which is smaller than a specimen to be measured, for example, an organic cell and the homogeneous part of the specimen is selected. Then, the light absorbancy As of the homogeneous part thus selected within the area of the light spot is measured. Substantially, the area of the cell S is measured and the total amount of the light absorbing substance of the specimen as a whole is obtained by the equation $M = As \times S$.

Such conventional one wave length and one region method has the disadvantage that if the light absorbing substance is not uniformly distributed in a specimen, for example, in an organic cell, the measurement error, so called distribution error caused by non-uniformity of the substance becomes large, and that since the area S of the specimen can only be measured in an approximate manner, the total amount M of the light absorbing substance becomes considerably erroneous.

The one wave length and two region method (2) makes use of a light spot which is smaller than the specimen and the transmittivity of that small light spot traversing the specimen is measured. This method also makes use of a large light spot externally contact with the specimen and the transmittivity of this large light spot traversing the specimen is measured. From here measured values, the light absorbancy of the light absorbing substance in the specimen as a whose is obtained by means of calculation treaties. In such conventional one wave length and two region method, certain conditions are required in order to satisfy the calculating equation. These conditions are less satisfied for the specimen used in practice. Thus, it is impossible to substantially decrease the distribution error of the light absorbing substance. As a result, such one wave length and two region method has the disadvantage that errors are introduced into the measured values, and that the adjustment for the size of the light spot is troublesome in operation and involves large personal errors.

The two wave length method (3) makes use of a light spot externally contact with specimen, for example, an organic cell and having two different wave lengths specially related each other. The specimen is irradiated by the light spots having these two wave lengths and externally contact with the specimen or cell to measure the transmittivities $T_1$ and $T_2$ with respect to the two wave lengths of the specimen and hence determine the total amount of the light absorbing substance in the specimen by means of calculating equations.

The two wave length method has been developed after completion of the Mendelszone's practical numerical value table which can be used for obtaining the light absorbancy of the light absorbing substance from the transmittivities $T_1$, $T_2$ with respect to the wave length. This method is capable of estimating the light absorbing substance in the specimen irrespective of the concentration distribution error in the specimen and of the size of the specimen. Thus, this method is convenient in practice.

In this conventional method, in case of selecting the wave lengths, the absorbancy indexes $K_1$ and $K_2$ for the two wave lengths $\lambda_1$ and $\lambda_2$ are selected such that a relation of $K_1^2 = K_2$ is given. For this purpose, that part of the specimen at which the light absorbing substance is uniform is selected and then an absorption spectrum curve is plotted. From this curve are determined a wave length $\lambda_1$ at which the light absorbancy is maximum and another wave length $\lambda_2$ at which the light absorbancy is ½ the maximum value, respectively. This conventional method, however, has the following disadvantages.

1. The size of the light spot must be changed every time the measurement is effected in accordance with the change of size of the specimen. The measurement of the size of the light spot is difficult and troublesome.

2. It is necessary to make the wave length of the light spot precise and uniformly irradiate the specimen by means of the light spot, otherwise involves measurement errors.

3. In case of selecting the wave lengths, it is necessary to select one wave length at which the light absorbancy is maximum and another wave length at which the light absorbancy is ½ the maximum value with the utmost care, because the erroneous selection of the wave lengths results in a considerably large measurement error.

4. The light loss produced by the light diffusion not peculiar to the specimen and caused by light reflection, refraction and diffraction in the specimen, if present, could not be detected nor corrected by this method.

In the two wave length method, the light spot is of large so that the Planck's measurement must be effected at the glass surface where that part of the specimen which is to be measured is absent. In case of the organic cell, for example, the light loss not peculiar to the protoplasm structure such as cytoplasm, nucleus and the like which is not taken into consideration for the Planck's measurement becomes contaminated.

As described above, the conventional two wave length method is very troublesome in the measuring operation and is in need of obtaining the total amount of the light absorbing substance in the specimen with the aid of the light transmittivity of the light spot having the two wave lengths by visually observing the numerical table, and as a result, it is very difficult to automatically effect the measuring operation. In the one wave length, scanning and integration method (4), that part of the specimen which is to be measured is divided into minute sections as small as possible such that the light absorbing substance in the divided minute section is considered to be uniformly distributed therein. The light absorbancy is measured in each minute section and this measuring operations are repeated over all of the sections to obtain measured values. Then, the total sum of these measured values is determined. That is, this conventional method consists in that part of the specimen which is to be measured is divided into very minute sections and then the specimen is moved in relative to the light spot to scan the specimen with the light spot and obtain a light absorbancy curve every time the scanning is effected. This light absorbancy curve is integrated to measure the light absorbancy for each scanned part of the specimen and the amount of the divided light absorbing substance. This measurement is effected all over the sections. These amounts thus obtained are summed up to obtain the amount of light absorbed by the specimen as a whole. This method effects an integration for the purpose of obtaining the light absorbancy of each of the scanned parts. As a result, it is possible to precisely obtain the measured value without contaminating any distribution error caused by the distribution irregularity of the light absorbing substance.

This method is ideal in principle and in practice in order to measure the amount of light absorbed by the light absorbing substance at that part of the specimen which is to be measured.

In this one wave length, scanning and integration method, however, the light deviation from the light path is lost in the space of an objective lens owing to the light diffusion caused by the reflection, refraction and diffraction of light in the specimen. As a result, the apparent light absorbancy becomes increased and hence the amount of light absorbed by the light absorbing substance is erroneously observed as if it were large.

This method has the disadvantage that the error produced by the light loss caused by not peculiar to the specimen is contaminated into the measured value. As a result, it is difficult to measure the true amount of light absorbed by that part of the specimen which is to be measured and precisely measure the amount of light absorbing substance contained in that part of the specimen which is not to be measured.

An object of the invention is to obviate the various disadvantages of the above described conventional method of microspectrophotometrically measuring light absorbancy of a specimen and provide a two wave length, scanning and integration type method of microspectrophotometrically measuring the light absorbancy of the specimen which can obviate the distribution error produced by the distribution irregularity at various places of the light absorbing substance in the specimen, which can obviate the error produced by the light diffusion due to the reflection, refraction and diffraction of light in the specimen, which can directly obtain the true amount of light absorbed by the specimen without using calculation treaties or without referring to numerical value table, and which can be effected by automation and hence remove the personal error.

Another object of the invention is to provide a microspectrophotometer for automatically carrying out the two wave length, scanning and integration type method of microspectrophotometrically measuring the light absorbancy of a specimen, which can automatically obtain the measured results in an efficient and precise manner.

A feature of the invention is the provision of a two wave length, scanning and integration type method of microspectrophotometrically measuring the light absorbancy of a specimen, comprising dyeing a specimen with a coloring matter, selecting a light spot having a wave length $\lambda_1$ at which a light absorbancy peculiar to said coloring matter is maximum and a light spot having a wave length $\lambda_2$ deviated from the absorption spectrum of said coloring matter and distant apart from said wave length $\lambda_1$ by a least distance and at the wave length $\lambda_2$ the light absorbancy is zero, scanning that part of said specimen which is to be measured along the same scanning path by means of said two light spots, integrating a light absorbancy curve peculiar to said coloring matter, and subtracting the light absorbancy of the specimen traversed by the light spot having the wave length $\lambda_2$ from the light absorbancy of the specimen traversed by the light spot having the wave length $\lambda_1$, thereby subtracting the light absorbancy produced by the light loss not peculiar to the specimen and caused by the light diffusion due to light reflection, refraction and diffraction in the specimen from the light absorbancy peculiar to the specimen and obtaining the true light absorbancy in proportion to the amount of light absorbing substance at that part of the specimen which is to be measured.

The method of microspectrophotometrically measuring light abandancy of a specimen according to the invention is capable of moving the specimen with respect to a minute light spot and scanning the former by the latter, integrating the light absorbancy of each of these scanned minute parts of the specimen and obtaining the light absorbancy of said minute scanned part thus obviating the distribution error, the same light path being scanned by a light spot having two different wave lengths, and obtaining the difference between the light absorbancies obtained by scanning the light spot having two different wave lengths thus obviating the error produced light absorption not peculiar to the specimen and caused by the light diffusion due to light reflection, refraction and diffraction in the specimen.

In the conventional two wave length method, the two wave lengths $\lambda_1$ and $\lambda_2$ of the light spot are selected such that the light absorbancy indexes $K_1$ and $K_2$ at these two wave lengths $\lambda_1$ and $\lambda_2$ are given by $K_1^2 = K_2$. On the contrary, the present invention permits of measuring the absorption spectrum of the coloring matter and of selecting the wave length $\lambda_1$ at which the light absorbancy of the absorption spectrum of the coloring matter is maximum and the wave length $\lambda_2$ at which the light absorbancy is zero and which is deviated from the absorption spectrum and located near the wave length $\lambda_1$.

In general, if the specimen is of organic such as cell and the like, use is made of Feulgen dyeing which can be bonded with the light absorbing substance in the specimen and in which the light absorbing substance is proportional to the light absorbancy of the specimen to be measured and which has a small proportionality error. In this case, the wave length $\lambda_1$ at which the light absorbancy peculiar to the coloring matter is maximum is selected to 550 m$\mu$ and the wave length $\lambda_2$ is selected to 450 m$\mu$.

In the conventional one wave length, scanning and integration method, the amount of light absorbed by each minute scanned part of the specimen is integrated to obtain the amount of light absorbing substance throughout the scanned parts of the specimen. For this purpose, the light penetrated through the specimen is incident on a photomultiplier tube by which the incident light is converted into an electric signal which after subjected to amplification and rectification is delivered to a recorder. The recorder can plot a light absorbancy curve on a record sheet. A number of square sections surrounded by each light absorbancy curve are counted to measure the area by which the value of the light absorbancy curve is obtained. These valves are summed up to obtain the light absorbancy of the specimen. Alternatively, the record sheet is cut out along each light absorbancy curve and the weight of the cut out portions is measured by a balance to obtain the integrated value of the light absorbancy curve. But, the operation of counting the sections of the record sheet or of cutting out the record sheet along the light absorbancy curve is very troublesome, takes a long time and involves an error.

Recently, it has also been proposed to microspectrophotometrically measure the light absorbancy of the cell for the purpose of measuring the amount of substance contained in the cell and of judging the abnormal condition of the cell so as to carry out a clinical examination. In such a case, it is particularly necessary to obtain the information with respect to the light absorbancy of the cell in a precise and rapid manner. Even in the foundation study and application study, it is beneficial to rapidly obtain the precise information with respect to the light absorbancy of the cell. Particularly, it is extremely important to precisely perform the quantitative measurement of organic and medical specimen such as nucleic acid DNA and the like of the cell.

Another feature of the invention is the provision of a two wave length, scanning and integration type microspectrophotometer comprising a specimen dyed with a coloring matter, a spectroscope including a driving device which can change over two kinds of wave lengths one from the other, at one of the wave lengths $\lambda_1$, the light absorbancy peculiar to said coloring matter being maximum and at another wave length $\lambda_2$ which is deviated from the absorption spectrum peculiar to said specimen the light absorbancy peculiar to said coloring matter being zero, a driving circuit for selecting the wave lengths of the light spot delivered from said spectroscope and controlling said wave length change over driving device, a stage for supporting said specimen and movable in X and Y directions, X-Y driving devices for moving said stage in X and Y directions, respectively, a photoelectric converter for converting the light traversing that part of said specimen which is to be measured into an electric signal, an integrator for integrating the electric signal delivered from said photoelectric converter, and a control circuit connected to said wave form change over driving device of said spectroscope, X-Y direction driving devices and integrator, respectively, and for controlling the wave length of the light spot delivered from said spectroscope in response to the operation of said X-Y direction driving devices, whereby that part of the specimen which is to be measured is scanned by said light spots having the wave lengths $\lambda_1$ and $\lambda_2$, respectively, along the same scanning path to control said integration such that the electric signal delivered from the photoelectric converter is separately integrated every time that part of said specimen which is to be measured is scanned by said light spots having the two wave lengths $\lambda_1$ and $\lambda_2$.

In case of effecting the microspectrophotometric measurement for the light absorbancy of the specimen according to the invention, in the first place, the absorption spectrum of the coloring matter is measured. Then, the wave length $\lambda_1$ at which the light absorbancy peculiar to the specimen is maximum and the wave length $\lambda_2$ which is deviated from the absorption spectrum of the coloring matter and distant apart from the wave length $\lambda_1$ by a least distance are selected. In case of measuring DNA of cell nucleus, for example, Feulgen dyeing in which the amount of the coloring matter to be bonded with DNA is proportional to DNA is selected. The wave length $\lambda_1$ at which the light absorbancy peculiar to this coloring matter is selected to 550 m$\mu$ and the wave length $\lambda_2$ deviated from the absorption spectrum is selected to 450 m$\mu$.

These wave lengths $\lambda_1$ and $\lambda_2$ can be automatically and repeatedly measured by presetting these wave lengths $\lambda_1$ and $\lambda_2$ to the circuit for controlling the spectroscope. If the range in which the specimen is scanned by the light spot is defined by the stage control circuit, the precise light absorbancy of that part of the specimen which is to be measured that is, the amount of light absorbed by that specimen portion can automatically and rapidly be measured in accordance with a program prepared beforehand and in accordance with which the wave length can be changed and specimen can be scanned.

The conventional scanning and integration type microspectrophotometer for measuring the light absorbancy of the specimen is troublesome in measuring operation and takes a time in calculating the measured data. Thus, it is only possible to effect the measurement of one or two specimens per one day with measurement error incurred.

On the contrary, the two wave lengths, scanning and integration type microspectrophotometer according to the invention is capable of precisely treating 50 to 100 specimens per one day, of automatically effecting the operation, and of precisely obtaining the true amount of light absorbed by the specimen. In addition, if the dyeing is determined beforehand, the two wave lengths $\lambda_1$ and $\lambda_2$ may be used without measuring them.

The invention will now be described in greater detail with reference to the accompanying drawings, wherein.

Figure 1:
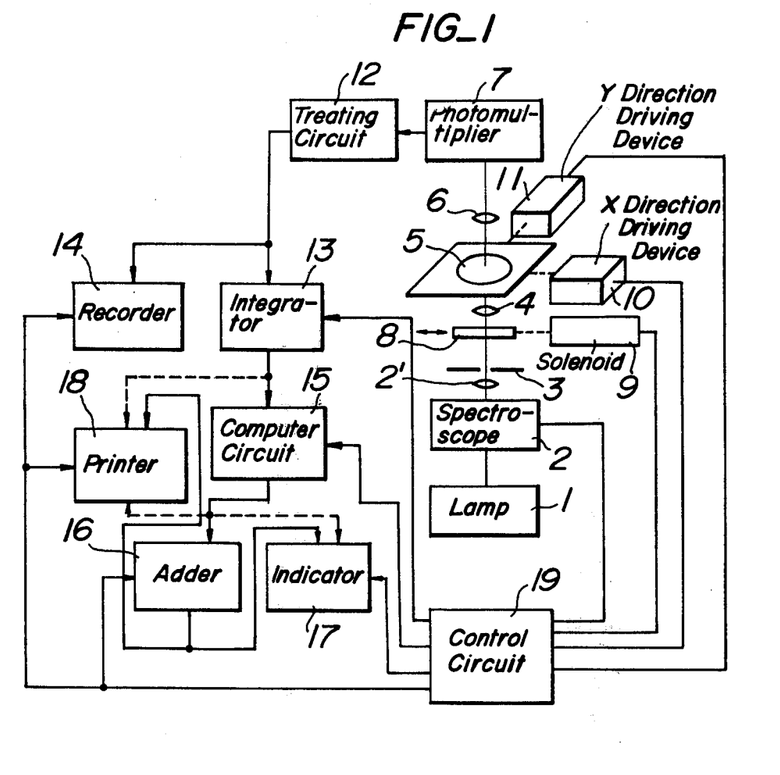
FIG. 1 is a block diagram showing one embodiment of a two wave length scanning integration type microspectrophotometer according to the invention.

Referring to FIG. 1, reference numeral 1 designates a lamp such as a tungsten or xenon lamp used as a stabilized light source. The light emerged from the lamp 1 is incident on a spectroscope 2. The spectroscope 2 is provided, for example, with a prism or diffraction grating which is made rotatable so as to change over the wave length of light traversing it. The image of the exit slit of te spectroscope 2 is formed on the position of the entrance pupil of a condenser lens 4 by means of a field lens 2'. Immediately after the field lens 2' is inserted a pin hole 3 whose reduced image is formed on the surface of a specimen disposed on a stage 5 by means of an objective lens 4 used as a condenser lens, the scanning stage 5 being movable in X and Y directions. The light emerged from the spectroscope 2 is a monochromatic light so that the reduced image formed on the surface of the specimen becomes a monochromatic light spot which is irradiated on that part of the specimen which is to be measured.

The light penetrated through the specimen is incident through an objective lens 6, which causes the specimen and the monochromatic light spot to be simultaneously magnified, on a photomultipler tube 7. The above described so-called Koana and Naora's optical system using the objective lens as the condenser and irradiating only that part of the specimen which is to be measured with the monochromatic light spot permits of measuring the amount of light absorbed by the local part of the specimen. Between the pin hole 3 and the condenser lens 4 is inserted a light screening plate 8 which is driven by a solenoid 9 such that the light screening plate 8 is inserted into and removed from the light path as shown by a double arrow. In addition, provision is made of an X direction driving device 10 for moving the stage 5 in X direction and a Y direction driving device 11 for moving the stage 5 in Y direction.

The output from the photomultiplier tube 7 is delivered to a treating circuit 12 which is composed of an electric power source for supplying a high electric voltage to the photomultiplier tube 7, an amplifier for amplifying the output from the photomultiplier tube 7, and a rectifier circuit. The output from the treating circuit 12 is delivered to an integrator 13 and to a recorder 14 which can plot a curve showing the light absorbancy of the specimen on a record sheet. The output from the integrator 13 is delivered to a computer circuit 15 which can subtract the integrated value obtained by scanning the specimen by the light having a wave length $\lambda_2$ from the integrated value obtained by scanning the specimen by the light having a wave length $\lambda_1$. The output from the computer circuit 15 is delivered to an adder 16 which can sum up the amount of light absorbed by the specimen during all of the scannings to obtain total amount of light absorbed by the specimen. The output from the adder 16 is delivered to an indicator 17 which can indicate by numerals the total amount of light absorbed by the specimen, that is, the amount of light absorbing substance contained in the specimen. The output from the adder 16 is also delivered to a printer 18 which can print the total amount of light absorbed by the specimen. The indicator 17 is adapted to indicate the wave length $\lambda_1$ and $\lambda_2$ set beforehand. The amount of light absorbed by the specimen when it is scanned by the light spot having the wave length set beforehand is indicated by the indicator 17 and recorded by the recorder 14.

The difference between the amount of light absorbed by the specimen when it is scanned by the light spot having the wave length $\lambda_1$ and the amount of light absorbed by the specimen when it is scanned by the light spot having the wave length $\lambda_2$ during the movement of the stage 5 in the Y direction is indicated by the indicator 17 and stored in the adder 16. In addition, the output from the integrator 13 may be delivered to the printer 18 so as to print the amount of light absorbed by the specimen every time it is scanned by the two wave lengths $\lambda_1$ and $\lambda_2$ as shown by dotted lines.

Alternatively, the output from the computer circuit 15 may be delivered to the indicator 17 and printer 18 so as to numerically indicate and print the true amount of light absorbed by the specimen when it is scanned by the light spots having the wave lengths $\lambda_1$ and $\lambda_2$, respectively.

Provision is made of a control circuit 19 for controlling the operations of the respective parts of the above described microspectrophotometer. The control circuit 19 is connected to the spectroscope 2, solenoid 9, X and Y direction driving devices 10, 11, integrator 13, recorder 14, computer circuit 15, adder 16, and printer 18 so as to control these devices in association with each other.

The operation of the microspectrophotometer shown in FIG. 1 will be described with reference to FIGS. 2 to 4.

In the present embodiment, in the first place a standard specimen dyed with a coloring matter is prepared and this standard specimen is used to plot an absorption spectrum curve of the coloring matter.

For this purpose, the lamp 1 is ignited and the solenoid 9 is energized to remove the light screening plate 8 out of the light path. Under such condition, the standard specimen disposed on the stage 5 is seen to make both the specimen and the light spot in focus.

In this case, the stage 5 may manually be moved or may remotely be controlled with the aid of the X and Y direction driving devices 10 and 11. Then, a signal is delivered from the control circuit 19 to the spectroscope 2 to drive its prism or diffraction grating and hence continuously change over the wave length of the monochromatic light emerged from the spectroscope 2. At the same time, a signal is delivered from the control circuit 19 to the recorder 14 to operate it such that the absorption spectrum curve of the coloring matter of the standard specimen is plotted on a record sheet.

Figure 2:
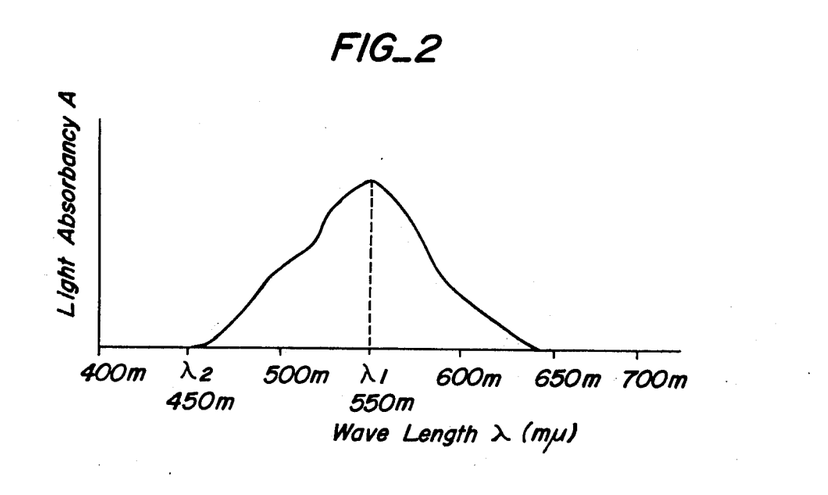
FIG. 2 is a graph which illustrates an absorption spectrum curve of a coloring matter.

In FIG. 2 is shown one example of the absorption spectrum curve plotted on the record sheet of the recorder 14. In the example shown in FIG. 2, use is made of Feulgen's dyestuff for dyeing the standard specimen and the wave length of the spectroscope 2 is changed over from 400 m$\mu$ to 700 m$\mu$. From this absorption spectrum curve is determined a wave length $\lambda_1$ (550 m$\mu$) at which the light absorbancy A is maximum and a wave length $\lambda_2$ (450 m$\mu$) at which the light absorbancy A is zero.

The wave lengths $\lambda_1$ and $\lambda_2$ determined as above described are preset in the control circuit 19 such that the monochromatic light of the wave length $\lambda_1$ and the monochromatic light of wave length $\lambda_2$ are repeatedly emitted from the spectroscope 2. In addition, the stage 5 is moved while the specimen is seen to locate the light spot at the position for starting scannings.

Figure 3:
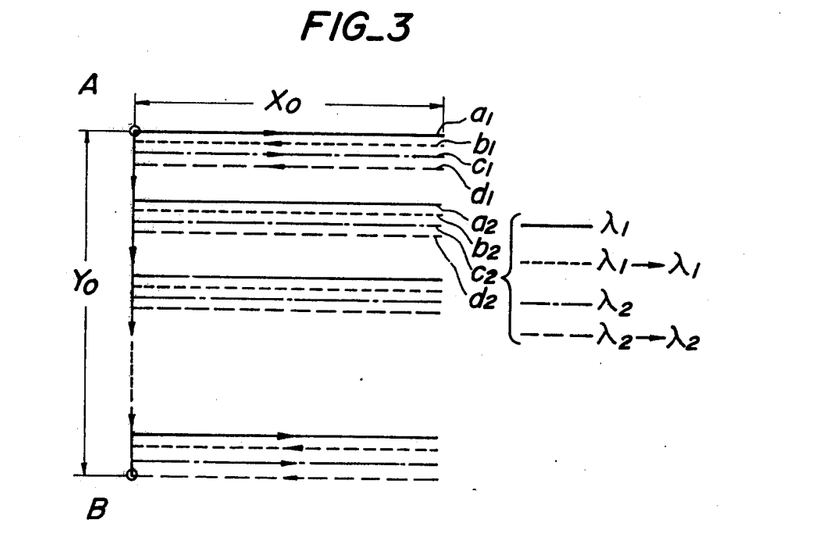
FIG. 3 is a diagram illustrating scanning paths of the microspectrophotometer shown in FIG. 1.

In FIG. 3 it is shown how to scan the stage 5 by the light spot. In FIG. 3, are shown scanning paths separately one from the other by a full line $a_1$ dotted lines $b_1$, dot and dash lines $c_1$ and dash lines $d_1$ for ease of illustration. In practice, however, these scanning paths travel the same path.

The size of the area to be scanned by the light spot is determined by dependence with the size of the specimen to be measured and the amount of movement $X_0$ in the X direction and the amount of movement $Y_0$ in the Y direction are preset in the control circuit 19, respectively. In the present embodiment, let the diameter of the light spot be 1 $\mu$, then it is possible to move the light spot up to 99 $\mu$ in the X direction and to move the light spot by a pitch of 1 $\mu$ up to 99 $\mu$ in the Y direction. As a result, the maximum scanning area is equal to 99×99 = 9801 $\mu^2$ and it is possible to scan the specimen by the light spot all over this area.

It is assumed that the light spot is located at a position for starting the scanning shown by a point A in FIG. 3, that a monochromatic light having a wave length $\lambda_1 =$ 550 m$\mu$ is emerged from the spectroscope 2, and that the solenoid 9 is deenergized to insert the light scanning plate 8 into the light path. If a start switch provided for the control circuit 19 is pushed at a time $t_0$ of the sequence table shown in FIG. 4, the solenoid 9 is energized by a signal delivered from the control circuit 19 to remove the light screening plate 8 out of the light path and the X direction driving device 10 is operated by another signal delivered from the control circuit 9 is to drive the stage 5 at a constant speed of 5 $\mu$/sec in the X direction. At the same time, the integrator 13 is also operated to integrate the signal delivered from the photomultiplier tube 7 and amplified by the treating circuit 12. At a time $t_1$ after the stage 5 has been moved by the amount $X_0$ preset in the control circuit 19, a stop signal is delivered from the control circuit 19 to the X direction driving device 10 to stop the stage 5 and at the same time deenergize the solenoid 9 to insert the light screening plate 8 into the light path, thereby screening the light. In addition, a signal is delivered from the control circuit 19 to the integrator 13 to stop the integrating operation and hold an integrated value $A\lambda_1$. Then, a signal is delivered from the control circuit 19 to the X direction driving device 10 to move the stage 5 in the opposite direction.

At a time a little later than the time $t_1$, from the control circuit 19 is delivered a pulse for sampling the integrated value to the integrator 13 to transfer the integrated value $A\lambda_1$ held therein to the computer circuit 15. At the same time, the integrated value $A\lambda_1$ is indicated by the indicator 17. Then, a signal is delivered from the control circuit 19 to the integrator 13 to reset it. The integrated value $A\lambda_1$ is accumulated in the computer circuit 15. The integrated value $A\lambda_1$ represents the amount of light absorbed by the specimen when it is scanned along the scanning path $a_1$ shown in FIG. 3 by the light spot.

During the light measurement along the scanning path $a_1$, the output from the treating circuit 12 is also delivered to the recerder 14 by which is plotted the light absorbancy curve obtained by the light measurement along the scanning path $a_1$ on the record sheet. In addition, the integrated value $A\lambda_1$ is also delivered to the printer 18 to print the integrated value $A\lambda_1$.

When the stage 5 is returned to the starting position A along the scanning path $b_1$, a signal is delivered from the control circuit 19 to the spectroscope 2 to change over the wave length of the light spot from $\lambda_1$ to $\lambda_2$.

Figure 4:
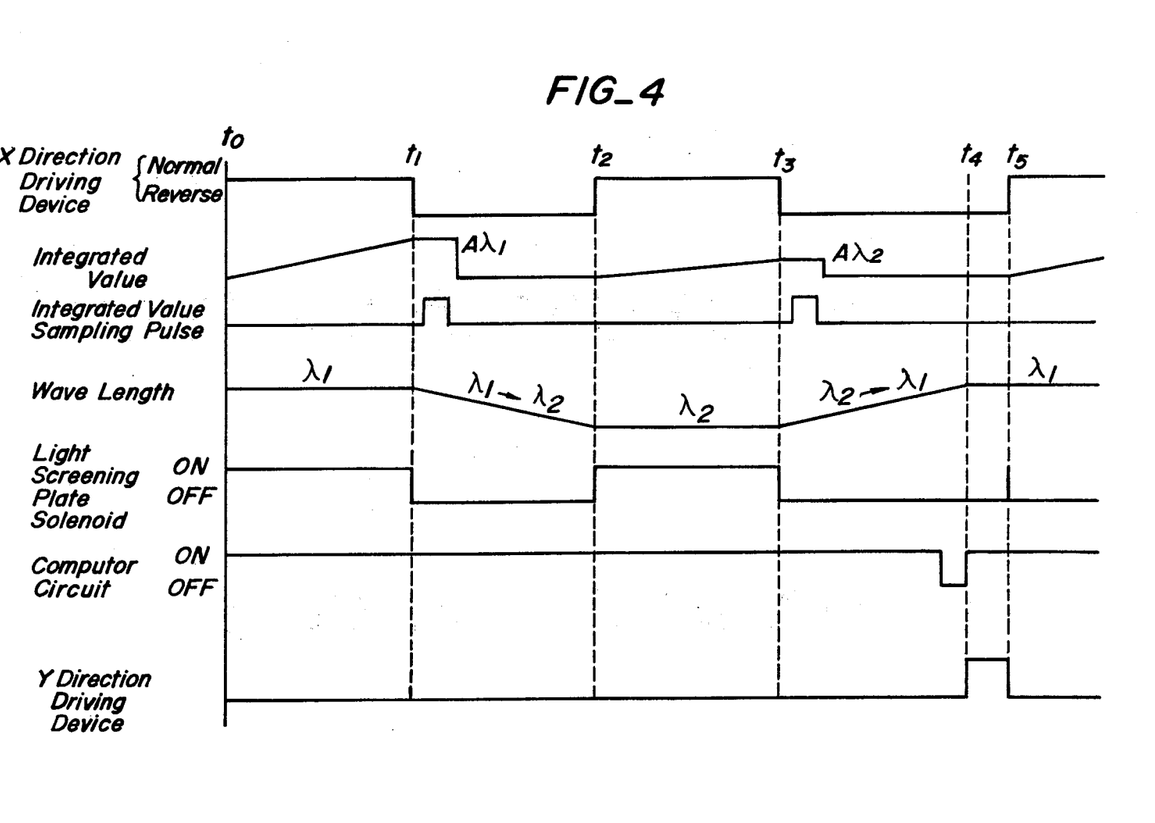
FIG. 4 is a table showing the sequence of operations of the microspectrophotometer shown in FIG. 1.

If the stage 5 is moved in the opposite direction by $X_0$ to the starting point A, a signal is delivered from the control circuit 19 to the X direction driving device 10 to stop the stage 5 at the time $t_2$ as shown in FIG. 4. Until the time $t_2$ the wave length of the light spot has been changed over from $\lambda_1$ and $\lambda_2$.

Then, a signal is delivered from the control circuit 19 to the solenoid 9 to remove the light screening plate 8 out of the light path. At the same time, a signal is delivered from the control circuit 19 to the X direction driving device 10 to move the stage 5 along the scanning path $c_1$. In the same manner as described above with reference to the scanning path $a_1$, the stage 5 is moved in the X direction by the distance $X_0$ during which the output from the photomultiplier tube 7 is integrated by the integrator 13.

As soon as the stage 5 has been moved by the distance $X_0$, at the time $t_3$, the X direction driving device 10 is stopped and the light screening plate 8 is inserted into the light path by means of the control circuit 19. In addition, the control circuit 19 causes the integrator 13 to stop its integrating operation to hold the integrated value $A\lambda_2$.

At a time a little later than the time $t_3$, a pulse for sampling the integrated value is delivered from the control circuit 19 to the integrator 13 to transfer the integrated value $A\lambda_2$ held by the integrator 13 to the computer circuit 15. After completion of the transfer of the integrated value $A\lambda_2$ from the integrator 13 to the computer circuit 15, the integrator 13 is reset to ready for the next operation.

At the time $t_3$ a signal is delivered from the control circuit 19 to the X direction driving device 10 to drive the stage 5 along the scanning path $d_1$ in the opposite direction. At the same time, a signal is delivered from the control circuit 19 to the spectroscope 2 to change over the wave length of the light spot from $\lambda_2$ to $\lambda_1$.

After the stage 5 has been moved along the scanning path $d_1$ in the opposite direction, at a time $t_4$ a signal is delivered from the control circuit 19 to the X direction driving device 10. While the stage 5 is returning along the scanning path $d_1$ to the starting position A, the computer circuit 15 is operated to subtract the amount of light absorbed by the specimen $A\lambda_2$ traversed by the light spot having the wave length $\lambda_2$ along the scanning path $a_1$ from the amount of light absorbed by the specimen $A\lambda_1$ traversed by the light spot having the wave length $\lambda_1$ along the scanning path $a_1$ to generate a true amount of light absorbed by the specimen $m_1$. That is, $m_1 = A\lambda_1 - A\lambda_2$.

This true amount of light absorbed by the specimen $m_1$ is delivered to the adder 16, to the indicator 17 to indicate it, and to the printer 18 to print it.

After completion of the above described computing treaties, a signal is delivered from the control circuit 19 to the computer circuit 15 to reset it.

At the time $t_4$, the wave length of the light spot has been changed over from $\lambda_2$ to $\lambda_1$ and the solenoid 9 has been deenergized. Then, a signal is delivered from the control circuit 19 to the Y direction driving device 11 to move the stage 5 in the Y direction by one pitch (in the present embodiment by 1 $\mu$).

At a time $t_5$, a signal is delivered from the control circuit 19 to the Y direction driving device 11 to stop the movement of the stage 5 in the Y direction. This time $t_5$ corresponds to the above described time $t_2$. From this time $t_5$, the same operation as the above described operation will be effected along the following scanning paths.

That is, the light is measured at the wave length $\lambda_1$ of the light spot along a scanning path $a_2$ to obtain the integrated value $A\lambda_1$. During the stage 5 is returned to the starting point A along the scanning path $b_2$, the wave length of the light spot is changed over from $\lambda_1$ to $\lambda_2$. In addition, the light is measured at the wave length $\lambda_2$ of the light spot along the scanning path $c_2$ to obtain the integrated value $A\lambda_2$. During the stage 5 is returned to the starting point A along the scanning path $d_2$, the wave length of the light spot is changed over from $\lambda_2$ to $\lambda_1$ and at the same time a subtraction is effected to obtain a true amount of light absorbed by the specimen $m_2 = A\lambda_1 - A\lambda_2$ along the second scanning path. This true amount of light absorbed by the specimen $m_2$ is delivered to the adder 16 and finally the stage 5 is moved in the Y direction by 1 $\mu$.

As seen from the above, the same measurements of light are effected along the successive scanning paths to obtain the true amounts of light absorbed by the specimen $m_1$, $m_2$ ... If the stage 5 has been moved in the Y direction by a distance $Y_0$ preset beforehand in the control circuit 19 and the measurement of light has been effected along the final scanning path, from the computer circuit 15 are delivered the true amounts of light absorbed by the specimens $m_1, m_2 \ldots m_n$ and from the adder 16 is delivered a total sum of the true amounts of light absorbed by the entire parts of the specimen $M = m_1 + m_2 + \ldots + m_n$.

This total sum of the true amounts of light absorbed by the specimen M is indicated by the indicator 17 and printed by the printer 18. Finally, the adder 16 is reset to complete the measurement.

The invention is not limited to the above described embodiment only and a number of modifications are possible. In the above described embodiment, the light absorbancy curve of the standard specimen is plotted to read out the wave length $\lambda_1$ of the light spot at which the amount of light absorbed by the specimen is maximum and the wave length $\lambda_2$ of the light spot at which the amount of light absorbed by the specimen is zero and these wave lengths $\lambda_1$ and $\lambda_2$ are preset in the control circuit 19.

As described above, these wave lengths $\lambda_1$ and $\lambda_2$ are determined by the kind of the coloring matters. Thus, it is possible to determine those wave lengths $\lambda_1$ and $\lambda_2$ of the light spot which are well matched with the coloring matter and effect interchange between these two wave lengths.

As seen from the absorption spectrum shown in FIG. 2, in the Feulgen's dyeing the absorption of light is not effected even at a wave length 650 m$\mu$, and as a result, it is possible to select the wave length $\lambda_2$ and 650 m$\mu$ in the red color region. The light energy at the wave length 650 m$\mu$ in the red color region is small in general and the photomultiplier tube 7 is less sensitive to the red color, so that it is preferable to use as the wave length $\lambda_2$ the wave length 450 m$\mu$ in the blue color region.

In the above described embodiment, while the wave length is turned over from $\lambda_1$ to $\lambda_2$ along the scanning paths $b_1$ and $b_2$ and from $\lambda_2$ to $\lambda_1$ along the scanning paths $d_1$ and $d_2$ the solenoid 9 is deenergized to insert the light screening plate 8 into the light path. The same effect may also be attained by an electronic switch connected between the photomultiplier tube 7 and the integrator 13 and by making this electronic switch OFF during the turn-over period between the wave lengths $\lambda_1$ and $\lambda_2$.

The photomultiplier tube 7 may be replaced by another photoelectric converter element such as a photoelectric cell, photodiode, phototransistor, photoconductive cell and the like. The photomultiplier tube, however, is most suitable viewed from the standpoint of its sensitivity and response time.

In the above described embodiment, the light spot is made stationary while the stage 5 for supporting the specimen is moved in X and Y directions. The specimen may be made stationary while the light spot may be moved in the X and Y directions. In addition, it is not always necessary to cause the relative movement between the specimen and the light spot to travel the scanning paths shown in FIG. 3. Various modifications are possible for the scanning paths.

Figure 5:
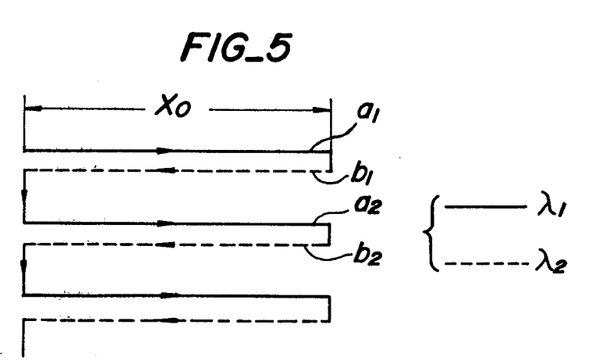
FIG. 5 is a diagram illustrating another example of the scanning paths shown in FIG. 3.

For example, the specimen may be scanned along the scanning path $a_1$ by the light spot having the wave length $\lambda_1$ and then the wave length may be changed over from $\lambda_1$ to $\lambda_2$. Then, the specimen may be scanned along the same scanning path $b_1$ in the direction opposite to the preceding direction. Then, the wave length of the light spot is turned over from $\lambda_2$ to $\lambda_1$ and the specimen may be scanned along the scanning path $a_2$ and then the specimen may be scanned along the same scanning path $b_2$ in the direction opposite to the preceding direction. The above operations are repeated to scan the specimen by the light spot having the wave lengths $\lambda_1$ and $\lambda_2$ along the same scanning path in the directions opposed from each other. In this case, the same scanning path is travelled by the specimen in directions opposed from each other so that the wave form depicted by the recorder 14 at the wave length $\lambda_1$ of the light spot is reversed to that at the wave length $\lambda_2$ of the light spot. But, the integrator 13 operates independently of the scanning directions so that the results obtained are the same. In this case, the same scanning path is reciprocated one time by the light spot, and as a result, the operation becomes relatively simple and the measuring time becomes shortened.

In this case, at the positions $X = 0$ and $X = X_0$, respectively, it is necessary to change over the wave length as well as stop the operation by a time during which the integrated value is treated. In the above described embodiment, these operations are effected while the stage 5 is returned along the scanning paths $b_1$ and $d_1$ to the starting position. Thus, it is not necessary to stop these operations at $X = 0$ and $X = X_0$, respectively.

It is also possible to effect the scanning by means of a light spot having both the wave lengths $\lambda_1$ and $\lambda_2$ and use may be made of two photoelectric converter elements each having wave length selecting property, and as a result, the amount of light absorbed by the specimen for the wave lengths $\lambda_1$ and $\lambda_2$ may simultaneously and separately be obtained. In this case, provision may be made of circuits for separately integrating the outputs from the two photoelectric converter elements, respectively. In addition, the output from the photoelectric converter element for the wave length $\lambda_1$ and the output from the photoelectric converter element for the wave length $\lambda_2$ may be delivered to a differential amplifier. In this case, provision may be made of one integrator for integrating the difference between these outputs so as to directly generate the integrated value representing the true amount of light absorbed by the specimen $m_1 = A\lambda_1 - A\lambda_2$.

Moreover, the output from the treating circuit 12 may be delivered to an electronic comparator by which integration, subtraction and addition are effected so as to obtain the true amount M of light absorbed by the specimen as a whole. In this case, the electronic computer may effect comparison between various kinds of data and the like so as to automatically treat the data.

What is claimed is:

1. A two wave length, scanning and integration type method of microspectrophotometrically measuring the total amount of light absorbed by a colored specimen, said method comprising:

moving said specimen disposed on a movable stage in X and Y directions, sequentially scanning a part of said specimen along the same path in the X direction by means of two light spots having wave length $\lambda_1$, $\lambda_2$ whose light absorbancies to the color of the specimen are maximum and minimum, respectively, changing over the wave length $\lambda_1$ to the wave length $\lambda_2$ and vice versa, screening the light path during said changing over operation, detecting the light transmitted through the specimen and generating an electrical signal indicative of the light absorbancy of the specimen, integrating said signals indicative of the light absorbancy every one scanning step to obtain the amount of light absorbed by said part of the specimen, accumulating said signals to determine the amount of light absorbed by said part of the specimen every one scanning step, subtracting the accumulated signals to determine the amount of light absorbed by said part of the specimen at the wave length $\lambda_2$ from the amount of light absorbed by said part of the specimen at the wave length $\lambda_1$ to obtain the true amount of light absorbed by said part of the specimen, accumulating the signals indicating said true amount of light absorbed by said part of the specimen, repeating said scanning every scanning line after successive movements of the stage in the Y direction to obtain signals representing true amounts of light absorbed by all parts of the specimen, and adding all of said signals representing true amounts of light absorbed by all parts of the specimen to obtain signals representing the total amount of light absorbed by said specimen.

2. A two wave length, scanning and integration type microspectrophotometer for measuring the total amount of light absorbed by a colored specimen, comprising:

a control circuit means connected to said control circuit for moving said specimen in X and Y directions, means for producing light spots having wave lengths $\lambda_1$, $\lambda_2$ whose light absorbancies to the color of the specimen are maximum and minimum, respectively, means connected to said control circuit for sequentially scanning a part of said specimen along the same path in the X direction by means of said light spots and changing over the wave length $\lambda_1$ to the wave length $\lambda_2$ and vice versa, means connected to said control circuit for detecting the light transmitted through the specimen to produce an electrical signal indicative of the light absorbancy of the specimen, means connected to said control circuit for screening the light path during said changing over operation and during movement of the specimen in the Y direction means connected to said control circuit for integrating the signals indicative of said absorbancy every one scanning step to obtain signals representing the amount of light absorbed by a part of said specimen, means connected to said control circuit for accumulating said signals representing the amount of light absorbed by said part of the specimen every one scanning step and for subtracting the signals representing the amount of light absorbed by said part of the specimen at the wave length $\lambda_2$ from the signals representing the amount of light absorbed by said part of the specimen at the wave length $\lambda_1$ to obtain signals representing the true amount of light absorbed by said part of the specimen, and means connected to said control circuit for accumulating said signals representing the true amount of light absorbed by the specimen and for adding all of said signals representing the true amounts of light absorbed by all parts of the specimen obtained by repeating said scanning every scanning line to obtain signals representing the total amount of light absorbed by said specimen.

* * * * *